(12) United States Patent  
Christy

(10) Patent No.: US 6,234,977 B1
(45) Date of Patent: May 22, 2001

(54) VARIABLE-FORCE MONOFILAMENT SENSORY DEVICE AND METHODS OF USING SAME

(76) Inventor: Michael Christy, 2108 Raven Rd., Pleasanton, CA (US) 94566

( * ) Notice: Subject to any disclaimer, the term of this patent is extended or adjusted under 35 U.S.C. 154(b) by 0 days.

(21) Appl. No.: 09/493,992

(22) Filed: Jan. 28, 2000

(51) Int. Cl.[7] ................................................. A61B 19/00
(52) U.S. Cl. ............................................. 600/557; 600/587
(58) Field of Search ................................. 600/553, 557, 600/587

(56) References Cited

U.S. PATENT DOCUMENTS

| D. 358,169 | * | 5/1995 | Osada | D19/53 |
|---|---|---|---|---|
| 2,704,539 | * | 3/1955 | Fisher | 600/557 |
| 3,662,744 | * | 5/1972 | Low et al. | 600/557 |
| 4,313,446 | * | 2/1982 | Kanatani | 600/553 |
| 4,641,661 | * | 2/1987 | Kalarickal | 600/557 |
| 4,964,412 | * | 10/1990 | Kelly | 600/557 |
| 5,316,011 | * | 5/1994 | Weinstein et al. | 600/557 |
| 5,823,969 | * | 10/1998 | Christy | 600/557 |

OTHER PUBLICATIONS

Smith & Nephew packaging insert for Retractable Monofilament product—10g #66000533: Jun. 1998.

* cited by examiner

Primary Examiner—Cary O'Connor
Assistant Examiner—Charles Marmor, II
(74) Attorney, Agent, or Firm—Malcolm B. Wittenberg

(57) ABSTRACT

The present invention relates to a device for delivering single point pressure sensations to a subject, to provide not only tactile sensory forces, but also precise gradations of these forces in a single hand-held unit. The operator can, by watching for the beginning of a bend in the monofilament probe, know exactly when the proper pressure for the test in progress has been applied. The device further comprises means to vary the angle at which the monofilament is delivered relative to the body portion by providing a choice of interchangeable tip members. The device enables a wide useful range of standardized force reading while substantially reducing the number of components required to accomplish meaningful diagnosis.

3 Claims, 6 Drawing Sheets

VARIABLE-FORCE MONOFILAMENT SENSORY DEVICE AND METHODS OF USING SAME

TECHNICAL FIELD OF INVENTION

The present invention relates to a monofilament sensory device which is capable of delivering several pre-calibrated forces and to methods of making and using same. More particularly, the present invention relates to a new and improved sensory cutaneous nerve function evaluation device and to methods for testing the peripheral nerve sensory function. The device includes a filament which is pressed against the body surface of a subject at various preselected and calibrated pressures and measures the sensory nerve function of that subject by the subject's perceived recognition of the pressure applied by the filament.

BACKGROUND OF THE INVENTION

The present invention relates to a device designed to test the sensory nerve function of a patient who is suspected of having or has had sensory nerve damage and to compare the results to data obtained from normal, healthy subjects. Such sensory dysfunction is known to occur due to (1) trauma affecting the continuity of nerve fibers, (2) disease processes including leprosy, diabetes, multiple sclerosis, and (3) other diseases resulting in diminished nerve conductivity; and nerve compression syndromes. The data gained from evaluation with said monofilaments provides an indication of the degree to which nerve damage has progressed and/or the degree to which recovery has occurred. Data thus obtained can be used to determine appropriate medical and/or surgical treatments to alleviate nerve compression or other causes of interference. Data can also be utilized in assessing the success of therapies and therapeutic modalities directed towards aiding in the restoration of nerve function or adaptation to nerve dysfunction. The readings provide an indication of the degree of damage to the patient's sensory nerves and/or a measure of recovery from damage to the patient's sensory nerves.

Filament testing has long been used as a sensitive monitoring means for evaluation peripheral nerve function of a patient. In the 1800's, the focus of peripheral nerve testing of the hands was carried out in a study of normal physiology using horse hairs as the filaments. In the late 1950's, it was determined that a broader range of filament forces were needed than those available with horse hairs to refine the filament method for peripheral nerve testing. Thus, J. Semmes and S. Weinstein developed and published results of testing cutaneous sensory perception using nylon monofilament rods of varied diameters and consistent tips and further published methods of using those rods to apply force. The nylon filaments were affixed to plastic rods (or "filament handles") which were cut to the approximate length of a pencil for ease of handling and comfortable fit in the therapist's hand. The devices were known as "aesthiometers". The advantage of these new filaments, when affixed to a plastic rod, was their ease of handling and their ability to create a range of testing values by varying the diameter of the filament affixed to a rod. These monofilaments attached to plastic rods with glue, came to be know as "Semmes-Weinstein monofilaments" and became the standard means for repeatable testing and measurement of the threshold of cutaneous sensory perception.

The standard Semmes-Weinstein approach suffered from the fact that it required a set of twenty (20) different monofilament rods of varied diameters in order to provide an effective diagnostic technique. Each nylon monofilament was about 38 mm in length and had diameters selected to correspond to Log (10×force in mg) of forces ranging from 4 mg (the lowest) to 447 grams (the highest). Furthermore, virtually all Semmes-Weinstein devices employed nylon monofilaments and, nylon was found to suffer from certain drawbacks which reduced the overall efficiency of the cutaneous sensory perception-measuring device.

The proper force for determining the patient's sensory perception is obtained at the moment the monofilament bends. The fragile nature of the nylon filament requires that it be carefully handled and stored. If the monofilament is misused or mishandled, a non-elastic deformation or kink can occur. Once such a kink occurs, the standard predictable moment of force required to form a uniform bend in order to make a peripheral nerve function determination is lost. Also, properties of nylon are subject to change with climatic changes which further reduces the predictability of the force required to cause the nylon monofilament to bend. Still another impediment, as stated above, is that the diagnostician, in order to perform a complete diagnosis, using the Semmes-Weinstein approach, had to carry twenty (20) monofilaments of varying diameters at all times.

A variety of handle designs have been considered the past decades in an attempt to provide a more convenient evaluation device. These designs include a single handle having five (5) monofilaments attached thereto and radiating therefrom and which rotate on the handle by means of a screw which tightens and loosens the monofilament rack on the handle (See: U.S. Pat. No. 5,381,806, Weinstein, et al.) This design was awkward to use when attempting to apply force against those areas of skin which may be difficult to reach such as the palm of a hand when that hand is held in a fist position or any other body parts that may be contracted in abnormal postures because, in attempting to contact the skin with only one point of a single filament, contact is often made by the non-selected filaments with adjacent body parts thereby negating the single stimulus response of the patient. These multi-filament handles also used nylon filaments which have the disadvantages noted above and additionally, requires that the entire set be replaced when even a single monofilament becomes unusable because of deformation or failure.

More recently, the use of alternative filament materials such as steel, were employed in the belief that they would enhance the accuracy of pressure aesthiometers by providing a force which is consistent over time and which is capable of providing a consistent footprint of area of stimulus. The steel wire pressure aesthesiometer presented by Kanatani in U.S. Pat. No. 4,313,446 provided an instrument purportedly capable of delivering such variable forces but had the distinct disadvantage of utilizing an exposed filament which was subject to deformation if not properly stored, and which required the interchange of filaments of varying diameters to provide for a full range of testing. Furthermore, steel has limited elastic properties and therefore is subject to inelastic bending. In such cases, the accuracy of force delivery is compromised resulting in a deviation from known clinical protocols.

The Kanatani design further required a deflection gauge upon which the diagnostician had to rely in order to achieve the desired range of filament deflection required to apply a promised force in grams of pressures. From the table given in FIG. 9 of the Kanatani patent (U.S. Pat. No. 4,313,446), it can be seen that in the smaller diameter filaments, a variance in deflection as small as 2.5 mm results in a 175% increase in the stress applied as measured in grams per square millimeter and a deflection variance of 10 mm will result in a 235% increase in the stress applied as measured in grams per square millimeter.

Thus, a major clinical disadvantage of the design proposed by Kanatani is that an evaluator must be ever alert to the area being tested and to the graph attached to the instrument indicating the degree of deflection. Tests of cutaneous sensory perception require care and precision to perform accurately and attention to the area of applied force is required particularly with persons who have known sensory dysfunction. Alteration of sympathetic function including sudomotor, vasomotor and pilomotor function, often result in trophic changes in affected areas. The result of these trophic changes may include loss of sweat patterns and skin dryness due to loss of the normal nutritive process of the skin. Skin may become thin and smooth and testing must be performed with caution and attention to prevent filaments from sliding or skipping on the skin which, if it occurs, will negate the single footprint stimulus required for objective evaluation. Control of the variables involved in testing to the extent possible reduces the subjectivity inherent in evaluation of the perception of a stimulus. Monitoring both the area and application of the stimulus and the instruments' deflection graph is clinically undesirable. In addition, the Kanatani instrument also required a bulky protective carrier and was not designed to provide convenience of use.

Other existing apparatuses used for the same and similar purpose as the Semmes-Weinstein devices employed a plurality of nylon filaments grouped into holders which provide multiple forces depending upon the filament chosen. These devices are awkward to use and bulky to store and carry, and do not permit truly accurate peripheral nerve testing of patients who have or who are recovering from sensory nerve damage. A substantially complete description of the art to which this present invention pertains can be found in "Somatosensory Occupational Therapy Association, Inc., Bethesda, Md. in 1977.

In spite of the various advances occurring through the years, as herein described, a clear need still exists for a new and improved monofilament sensory device which overcomes the significant deficiencies in the prior art which is readily portable and is capable of creating reproducible results irrespective of circumstances. It is toward these goals that the present invention is directed.

It is thus an object of the present invention to provide a hand-held single-point sensory evaluation device which eliminates the need for inventorying multiple evaluation tools, provides a consistent calibrated force over the entire range of desired testing, is clinically useful and substantially reduces the subjectivity in the evaluation of sensory nerve function.

A further object of the present invention is to provide a single tool which is easily held in the palm of the hand and which provides a multiple selection of precise forces to be applied to a patient utilizing a single monofilament, braid or wire.

A still further object of the present invention, is to provide unique means and methods for determining a precisely calibrated force or pressure over an entire continuous range not limited to pre-selected end point values at the end of the monofilament when that monofilament is pressed against the skin of the test subject until the filament bows.

Still another object of the present invention is to provide a single handheld instrument that reduces the variables involved in determining the calibrated force application to the single variable of filament deflection as a factor of force or pressure.

A still further object of the present invention is to provide an instrument that complies with clinically valid constructs whereby the instrument delivers a sensory filament at a 90-degree angle to the handle and can be further modified to deliver "ergonomically sensitive" angles for applications not yet clinically validated.

These and still further objects, as shall hereinafter appear, are readily fulfilled by the present invention in a remarkably unexpected manner as will be readily discerned from the following detailed description of exemplary embodiments thereof especially when read in conjunction with the accompanying drawings in which like parts bear like indicia throughout the several views.

SUMMARY OF THE INVENTION

The present invention relates to a hand-held single point aesthiometer provided with a plurality of monofilaments which provide variable settings designed to test for nerve sensory function. For a monofilament of a given diameter, the length of the monofilament extending from one end of a handle of the present invention determines the amount of force which can be delivered at the end of the filament when it is placed in contact with the skin of the subject and pressed. The device can be employed at various angles between the monofilament and the base or handle and utilizes a unique correlation between the length of the filament extension and the diameter of the filament to obtain a useful range of responses while substantially reducing the number of components required to accomplish a meaningful diagnosis.

Accordingly, a primary object of the present invention is to provide an aesthiometer for carrying out the Semmes-Weinstein type of sensory perception procedure in which the multiplicity of devices heretofore required by the prior art are eliminated or substantially reduced and an entire range of desired testing is achieved by a single hand-held instrument armed with substantially fewer monofilaments than has been heretofore required.

DESCRIPTION OF THE PREFERRED EMBODIMENT

Figure 1:
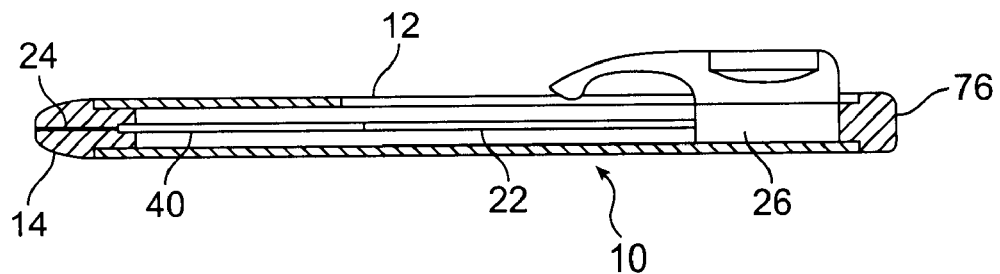
FIG. 1 is a side view, partially in cross-section, showing one embodiment of the present invention.

The present invention is a single-point S-W type device called an "aesthesiometer" having variable settings designed to test for nerve sensory function. As can be seen from FIGS. 1–3, the device, identified by the general reference 10, is constructed of two basic parts. The first of these is an elongated tubular body portion 12 and the second is an interchangeable tip member 14. Each body portion 12 has an internally threaded mouth 16 at one end thereof, a tip receiving opening 18 at the other end and a passageway 20 defined therein and extending between mouth 16 and opening 18 coaxially with the center axis of body portion 12.

Disposed within body portion 12 and coaxial with elongated passageway 20 is a metal monofilament holder 22 into which the desired monofilament 24 is inserted for purposes to be hereinafter described in detail. In one embodiment of the present invention, clip member 26 is provided with a first opening 28 for seating upon tubular body portion 12 and adapted to ride within a serpentine channel. Clip member 26 further comprises an axially extending seating means 32 which is defined therein for receiving and securing the proximal end 34 of monofilament holder 22 into which the pre-selected monofilament 24 is inserted. The distal end 36 of monofilament holder 22 is inserted into the proximal end 38 of metal alignment tube 40 which is likewise disposed within passageway 20 to facilitate the delivery of monofilament 24 to and through tip member 14 and out of opening 42 for use in the manner to be hereafter described.

Once the body portion 12 is filled with the desired monofilament holder 22 in which the pre-selected monofilament 24 is seated, and monofilament 24 is guided into alignment tube 40, the tip member 14 of choice is secured in tip receiving opening 18, and end cap 76 is seated in mouth 78 of passageway 20 to prevent the entry of foreign matter into device 10.

In a first embodiment, each tip member 14 comprises a tip body portion 44 having a threaded neck portion 46 for threaded engagement within tip receiving opening 18 of body portion 12 and a passageway 48 extending through body portion 44 for guiding monofilament 24 when it is desired to extend monofilament 24 out of body portion 12 for diagnostic use. Passageway 48 leads to egress port 50 disposed on the distal surface 52 of tip body portion 44 from which monofilament 24 will extend when device 10 is being used. Tip member 14, as shown in FIGS. 1 and 2, delivers monofilament 24 on the central axis of passageway 20.

Figure 2:
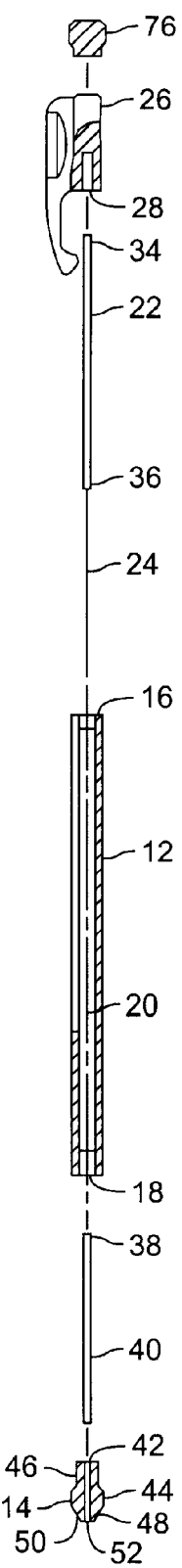
FIG. 2 is an exploded view partially in cross-section of the embodiment of FIG. 1.
Figure 3:
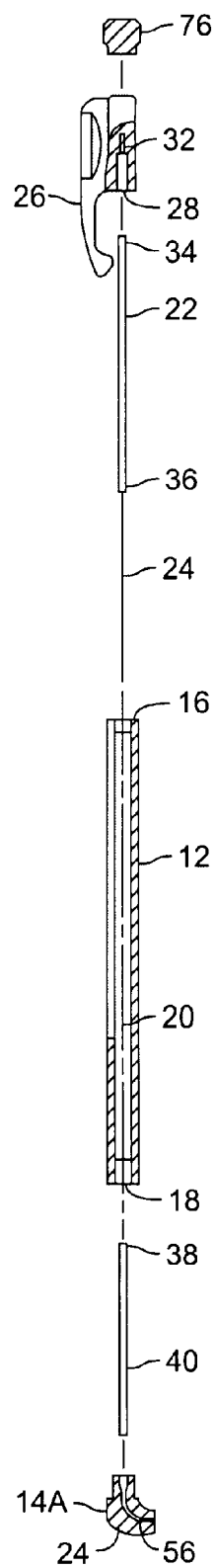
FIG. 3 is an exploded view partially in cross-section of another embodiment of the present invention.

As further embodiments as shown in FIGS. 2 and 3, tip member 14 is interchangeable with alternate tip member 14A and 14B, the differences between which will now be described.

The first alternative 14A as shown in FIG. 3, comprises a tip body portion 54 having a curvilinear passageway 56 passing therethrough to deliver monofilament 24 toward the patient at an angle of approximately 90° to the axis of main body portion 12. In most applications, as will hereinafter appear, tip member 14A will be the tip member of choice for most procedures.

Figure 4:
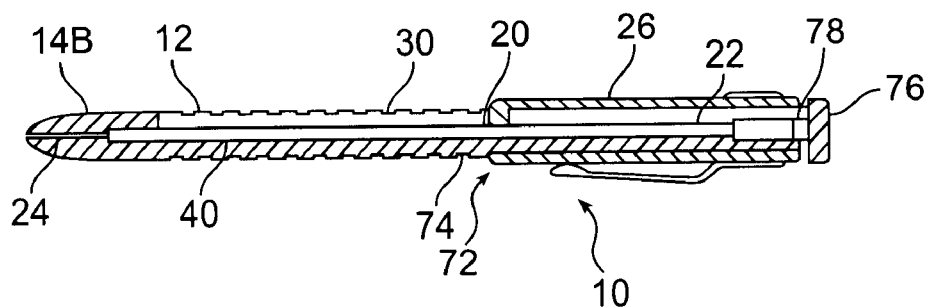
FIG. 4 is a cut-away view of the device showing an internal mechanism employed to adjust the extension of the monofilament wire to the desired length when in use and to its storage position, when not in use.
Figure 5:
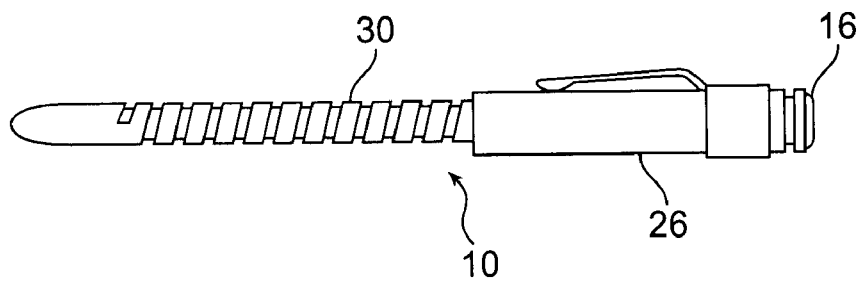
FIG. 5 is a side view, showing means for advancing and retracting the monofilament and monofilament holder.

The advance and retraction of the monofilament is described with reference to FIG. 4. Means 72 for advancing and retracting monofilament 24 along alignment tube 40 in passageway 20 to and through opening 18 comprises the coactive engagement of protrusion 74 of clip member 26 into serpentine channel 30 and advancing clip member 26 about body portion 12 which causes the axial movement of monofilament holder 22, which is seated through opening 28 in clip member 26 and moveable therewith, and hence the axial movement of monofilament 24 protrudes beyond tip member 14 to provide the desired target force. To retract the monofilament 24 after use, clip member 26 is simply rotated about body portion 12 in the reverse direction causing riding protrusion 74 to pass along channel 30 until monofilament 24 is out of sight.

In practice, the preferred monofilament wire will be made of nitinol or other materials having similar elastic qualities while the preferred material for the body portion is durable plastic. Nitinol is a well-known nickel-titanium alloy wire, which can be configured in various diameters and lengths to provide a known force at its tip when the monofilament wire starts to bend. Nitinol does not have any of the problems associated with the nylon filaments used currently.

Figure 6:
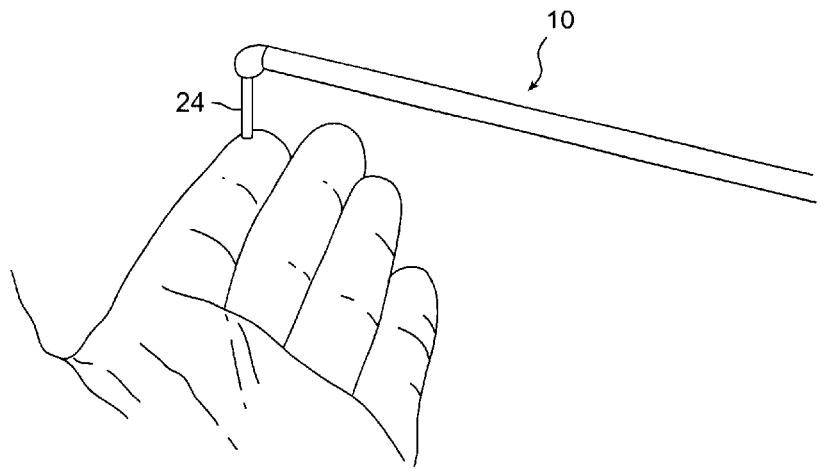
FIG. 6 is an isometric view of the present invention in use.

In manufacture, device 10 will be sized so that it can fit easily into the human hand. The user of the present invention, normally a health care provider such as a therapist or physician, will then adjust the length of monofilament wire extension from the case to the length corresponding to the force desired. The device is held in a cupped hand with the forefinger resting at the end of the pen-shaped case near the extruding end of monofilament wire and the thumb and second finger securing the device in the therapist's hand. The extruding end of monofilament wire is then applied to a desired point on the patient's skin so that at the moment of contact the monofilament wire is perpendicular to the skin. Pressure is applied along the axis of the monofilament wire until it just begins to bend as shown in FIG. 6. A different length/force setting will then be tried depending on whether or not the patient was able to perceive the pressures from the monofilament as set before.

The present invention brings many improvements to the art. For example, the device is easily portable and adjusts so as to replace the 20 S-W nylon filaments and holders previously necessary to conduct this type of sensory nerve test function. The device is shown as being pen-shaped although alternative handle shapes, such as those having flat and rectangular cross-sections, are contemplated. The present invention is clearly more portable and easier to use than the prior devices which combine sets of nylon filaments into more bulky devices.

A further principal benefit in practicing the present invention lies in this invention's unique ability to not only replicate the fixed forces of the individually preset prior art instruments but further apply forces that are between the values currently available. For example, at the 10 gram range used for diabetes diagnosis, a clinician would generally require access to a twenty-count set of instruments and would generally employ six different such instruments to deliver forces at 4, 6, 8, 10, 15 and 26 grams. Obviously, the present invention is capable of replicating each of the these forces while employing a single handle and single filament. In addition, the present invention can deliver intermediate forces such as 7, 9, 11, 12, 13, 14, etc. grams by choosing monofilament lengths as desired. This enables the clinician to not only fine tune the instrument beyond the capabilities of the prior art but can also extend the diagnostic value of the instrument by providing the clinician with a baseline to monitor a subject's progress by noting changes in sensory perception which may perhaps be less than the preset values of prior devices and thus not perceptable by such devices unless and until the subject has shown a change at least as great as the stepped delivery forces of those monofilament sensory instruments currently available.

In the preferred embodiment of the present invention, there can be as many as six different monofilaments within a single unit but, of course, only one is used at a time. Each monofilament is capable of providing multiple force readings depending on the length of the protrusion. In a typical situation, the inclusion of six monofilaments will provide a range in diameters of from 0.002 to 0.022 inches and the deliverable forces will range from about 25 mg to about 450 grams. The mid-range force will use 0.004 to 0.009 inch diameters and will vary in length from about 0.6 inches to 2.0 inches to deliver the target forces. The preferred embodiment of the present invention will deliver forces in 0.5 to 2 gram increments with precision.

Figure 7:
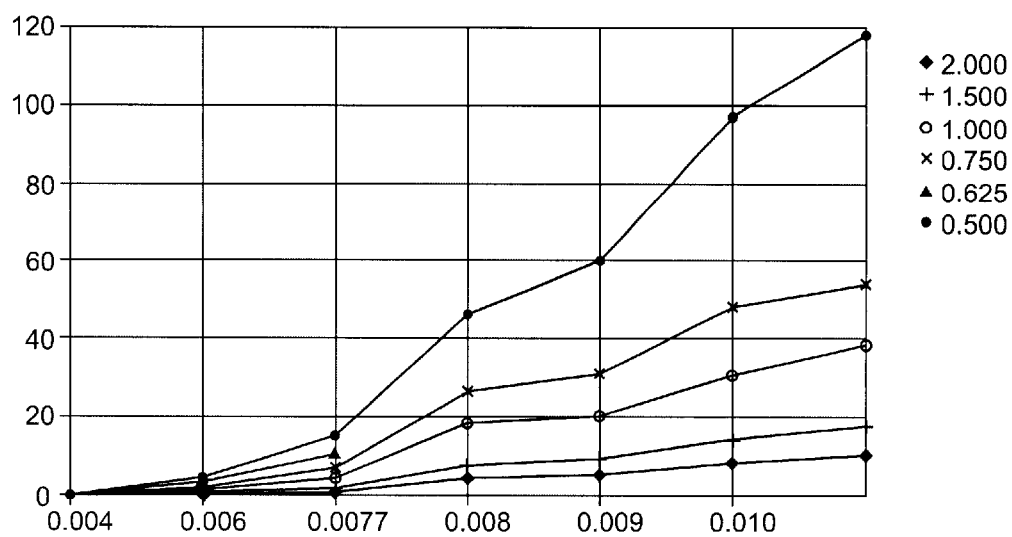
FIG. 7 is a graphical depiction relating the force delivered (in grams) as a function of the diameter of the monofilament (in centimeters) at diverse monofilament lengths.

A typical calibration curve for one of the diameters thus calibrated is shown below in FIG. 7. The graph depicts force delivered (in grams) as a function of the diameter of the monofilament (in cm) at diverse monofilament lengths.

In actual practice, monofilament diameters of 0.007 to 0.009 inches are especially useful for diagnosis associated with diabetic patients although the full range available will encompass sensory function testing. While any of the known monofilament material may be employed in the practice of the present invention, nitinol has been found especially desirable and offers physical properties not readily available from nylon as was explained above.

As shown in FIG. 6, the device is used by placing the subject's arm, finger or the like on a flat surface where it is engaged by the leading edge of monofilament 24 disposed normal to the surface being tested. The practitioner then gently bears down on the monofilament 24 until it bends.

As described above, the device 10 is calibrated so that monofilaments 24 will begin to deflect laterally and thereafter buckle in response to a predetermined reactive force applied thereto. Each monofilament 24 is capable of several different force values depending on how much of the monofilament protrudes from tip member 14.

Figure 8A:
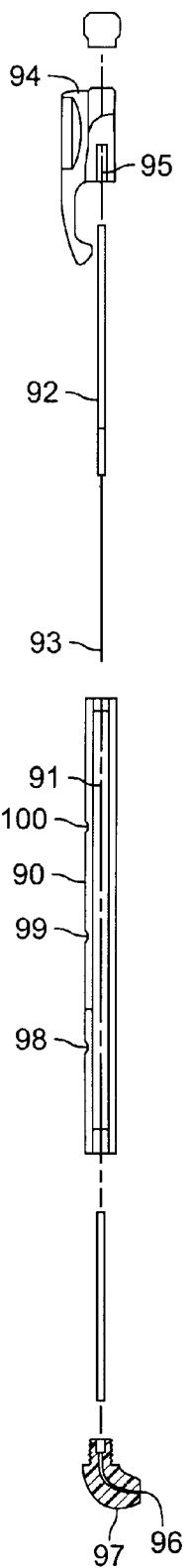
FIGS. 8A through C represent cutaway views of a further embodiment of the further invention whereby extending the monofilament is conducted by means of a sliding rather than helical rotating motion.
Figure 8B:
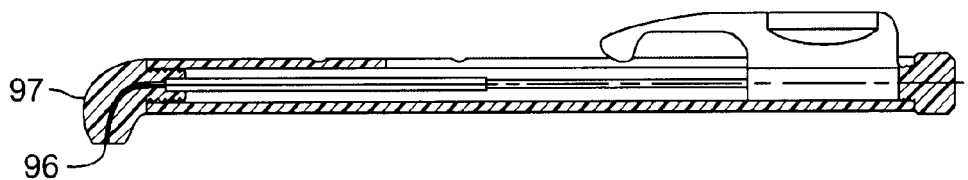
Figure 8C:
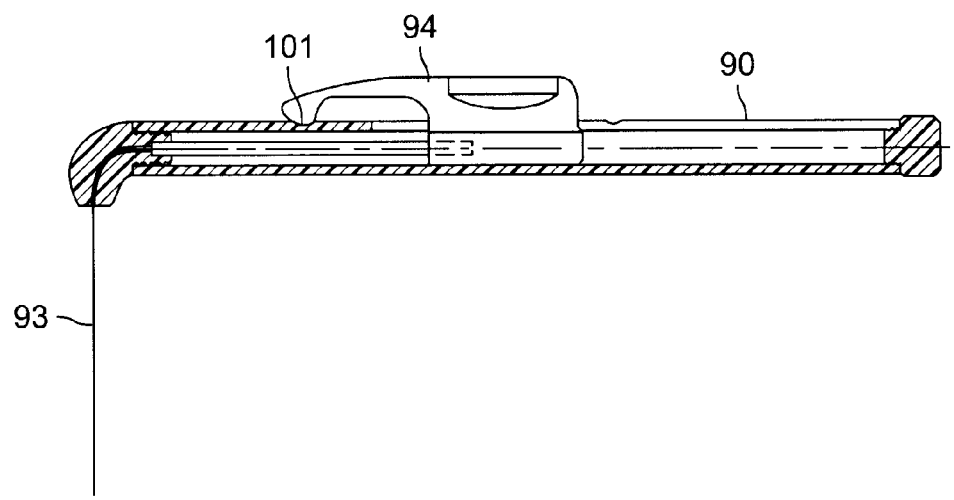

FIGS. 8A–C depict yet another embodiment of the present invention. In this instance, body portion 90 is shown with elongated passageway 91 including monofilament holder 92 into which the desired monofilament 93 is inserted. Monofilament holder 92 is frictionally inserted within pocket clip 94 at recess 95. Once assembled, monofilament 93 extends within channel 96 of tip 97 such that movement of clip 94 along the exterior of body portion 90 results in monofilament 93 extending beyond tip 97 as shown in FIG. 8C.

As noted, sensory force can be calibrated as a function of the length of monofilament 93 extending from tip 97 as well as the nature of the monofilament material itself. The device of the present invention is infinitely adjustable although preset sensory force values can be established through indents 98, 99, 100, etc. as clip portion 101 of clip 94 slidably engages each indent. To reiterate, however, the device of the present invention can be calibrated enabling a clinician to choose monofilament 93 protrusion beyond tip 97 as desired to select sensory force values in between those established by the indents. This provides a device having a flexibility unrecognized by competitive devices of the prior art.

In practice, M-value marking will be placed on the handle where: M=log (10×F) and F is the buckling force in milligrams; where the diameter of the monofilament 22 is known, the cross-sectional area may be easily calculated and the stress value obtained by dividing F by the area calculated.

In use, the procedure will be repeated with various monofilament diameters and extended lengths until the patient recognizes a clear sensation at the tested area at a level of applied force sufficient to cause the extended monofilament to buckle. The degree of stress at the tested skin area can then be determined by referring to the M-calibration chart or as optionally inscribed on the device related to the monofilament diameter used.

From the foregoing, it is readily apparent that a new and useful embodiment of the present invention has been herein described and illustrated which fulfills all of the aforestated objects in a remarkably unexpected fashion. It is, of course, understood that such modifications, alterations and adaptations as may readily occur to the artisan confronted with this disclosure are intended with the spirit of this invention which is limited only by the scope of the claims appended hereto.

What is claimed is:

1. A device for measuring peripheral nerve sensory response in a subject comprising a body portion forming a handle, a tip member, an elongated monofilament having predictable elastic properties and extended elastic memory disposed within said handle in substantially coaxial relationship thereto, and means for selectively extending said monofilament from said handle through said tip member and retracting said monofilament back into said handle to provide, when extended, a predetermined length of monofilament protruding axially from said tip member to a tip, said length being directly correlatable to a given point pressure when said tip is engaged with the subject in generally perpendicular relativity thereto and the handle is pressed until said protruding monofilament starts to bend wherein said device is provided with a serpentine channel defined in an outer surface of said body portion, a clip member disposed in circumscription about said body portion and having means extending therefrom for engagement with said channel, said clip member further included means for securing said monofiliment thereto for movement therewith when said clip is moved about said body portion and in said channel to advance and retract said monofilament relative to said body portion.

2. A device for measuring peripheral nerve sensory response in a subject comprising a body portion forming a handle, a tip member, an elongated monofilament having predictable elastic properties and extended elastic memory disposed within said handle in substantially coaxial relationship thereto, and means for selectively extending said monofilament from said handle through said tip member and retracting said monofilament back into said handle to provide, when extended, a predetermined length of monofilament protruding axially from said tip member to a tip, said length being directly correlatable to a given point pressure when said tip is engaged with the subject in generally perpendicular relativity thereto and the handle is pressed until said protruding monofilament starts to bend and wherein said device further comprises a detachable tip member having a curvilinear passageway defined therein for guiding said monofilament therethrough to an angle of 90 degrees relative to the central axis of the handle.

3. A device for measuring peripheral nerve sensory response in a subject comprising a body portion forming a handle, a tip member, an elongated monofilament having predictable elastic properties and extended elastic memory disposed within said handle in substantially coaxial relationship thereto, and means for selectively extending said monofilament from said handle through said tip member and retracting said monofilament back into said handle to provide, when extended, a predetermined length of monofilament protruding axially from said tip member to a tip, said length being directly correlatable to a given point pressure when said tip is engaged with the subject in generally perpendicular relativity thereto and the handle is pressed until said protruding monofilament starts to bend and wherein said body portion is provided with a series of indents and a clip member such that as the clip member engages said indents, a pre-determined length of monofilament is caused to extend beyond said tip member and wherein said body portion is further provided with a series of indicia correlating a length of monofilament extendable beyond said tip member with the clip member movable along said body portion.

* * * * *